United States Patent [19]

Nagy et al.

[11] Patent Number: 4,661,618
[45] Date of Patent: Apr. 28, 1987

[54] 1-3,BIS(DIMETHYLAMINO)-2-PROPYL-4-CHLOROPHENOXY-ACETATE, ACID ADDITION SALTS THEREOF, A PROCESS FOR THE PREPARATION OF THE SAME AND PHARMACEUTICAL COMPOSITIONS COMPRISING THE SAID COMPOUNDS

[75] Inventors: Imre Z. Nagy; Zsuzsanna Emri; Sandor Jancsó; István Csernus; János Bálint, all of Debrecen, Hungary

[73] Assignee: Biogal Gyogyszergyar, Debrecen, Hungary

[21] Appl. No.: 606,347

[22] Filed: May 2, 1984

[30] Foreign Application Priority Data

May 2, 1983 [HU] Hungary ................. 1496/83

[51] Int. Cl.$^4$ .......................................... C07C 69/76
[52] U.S. Cl. ......................................................... 560/62
[58] Field of Search ................... 560/62; 514/532, 534

[56] References Cited

FOREIGN PATENT DOCUMENTS 50-19541  7/1975  Japan ................................. 560/62
1288670  9/1972  United Kingdom ................. 560/62

Primary Examiner—Paul J. Killos
Attorney, Agent, or Firm—Karl F. Ross; herbert Dubno

[57] ABSTRACT

This invention relates to the new 1,3-bis-(dimethylamino)-2-propyl-4-chlorophenoxyacetate of the Formula (I)

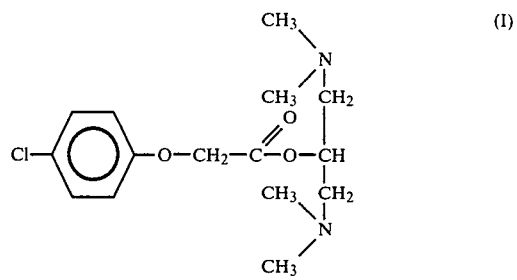

acid addition salts thereof, a process for the preparation of the same and pharmaceutical compositions comprising the said compounds.

The novel compound of the present invention corresponds to the Formula (I). This compound stimulates the function of the brain cells and thereby mental activity.

The compound of the Formula (I) can be prepared by esterifying (4-chlorophenoxy)-acetic acid or a functional reactive derivative thereof with 1,3-bis-(dimethylamino)-2-propanol or a halogeno derivative thereof in a manner known per se.

4 Claims, No Drawings

1-3,BIS(DIMETHYLAMINO)-2-PROPYL-4-CHLOROPHENOXY-ACETATE, ACID ADDITION SALTS THEREOF, A PROCESS FOR THE PREPARATION OF THE SAME AND PHARMACEUTICAL COMPOSITIONS COMPRISING THE SAID COMPOUNDS

FIELD OF THE INVENTION

This invention relates to the new 1,3-bis-(dimethylamino)-2-propyl-4-chlorophenoxyacetate of the Formula (I)

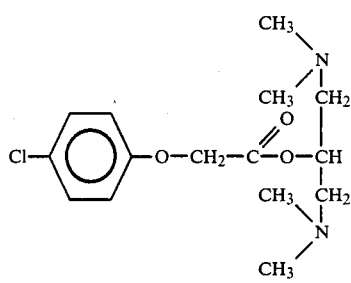

acid addition salts thereof, a process for the preparation of the same and pharmaceutical compositions comprising the said compounds.

The compound of the formula (I) and acid addition salts thereof are active as neurostimulants and are capable of preventing gerontologically induced loss of cerebral function.

BACKGROUND OF THE INVENTION

It is known that dimethylaminoethyl-4-chlorophenoxyacetate exhibits a memory and learning stimulateing, neuroenergetic effect [Martin Negwer: Organisch-chemische Arzneimittel and ihre Synonyma, Akademie-Verlag Berlin 1951 (1978)]. Pharmaceutical compositions comprising this compound (Centrophenoxin) are used in therapy as central stimulants [Arzneimittel Forschung 13, 881 (1963)]. Several procedures are known for the preparation of this compound. The majority of these processes are esterifying methods known per se [Czechoslovakian patent specification No. 154,866; Japanese patent application (KOKAI) No. 72-389386, British patent specification No. 954,196; DOS No. 2,006,338]. According to Japanese patent application (KOKAI) No. 75-19542 the ester obtained is subjected to subsequent chlorination. According to Japanese patent application (KOKAI) No. 75-19542 the desired compound can also be prepared by a reaction carried out with three components (4-chlorophenol, chloro acetic acid and 1,2-bis(dimethylamino)ethanol).

On studying the action of mechanism of the above compound it has been found that the said substance, originally known as neuroenergic agent, exhibits an effect on the ageing process of the cells as well. It has been found that the chronic treatment of aged animals with the compound decreased the ageing pigment content of the nerve cells of the brain and that of the myocardium [Nature 210, 313 (1966)], the lifespan of the animals significantly increased and the learning ability of the aged animals improved [Expl. Gerontol. 8, 185 (1973b)].

According to the hypothesis of the ageing of cells which explains this process with a theory connected to the membrane, the first stage of the ageing of postmitotic cells resides in a decrease of the passive potassium permeability of the cell membranes which is probably the result of the cross binding ability of the aggressive free radicals formed during cellular respiration [J. Theor. Biol. 75, 189 (1978): Mech. Age. Dev. 9, 237 (1979)]. The substituted amino group of the said known compound exerts in vitro a significant radical neutralizing effect being probably in connection with the electrone delivering character of the nitrogen atom [Mech. Age Dev. 14, 245 (1980)].

The nitrogen containing esters of 4-chlorophenoxyacetic acid known from prior art—i.e. Centrophenoxin—comprise a substituted amino group [Bull. Soc. Chim. France 1960; 1786; Biol. Aktiv Soedin 1965, 112; C. A. 63, 179480 (1965)].

DESCRIPTION OF THE INVENTION

The present invention is based on the discovery that the dimethylaminoethanol moiety of the molecule of the Centrophenoxin is intussuscepted into the brain-tissue and neutralizes the free radicals. We have found that two amino groups are more active than one and by synthesizing an analogous compound containing two substituted amino groups a therapeutical agent being more effective against the ageing process of the cells can be obtained.

According to a feature of the present invention there is provided a novel compound, 1,3-bis(dimethylamino)2-propyl-4-chlorophenoxyacetate of Formula (I) and acid addition salts thereof.

According to a further feature of the present invention there is provided a process for the preparation of the compound of the Formula (I) and acid addition salts thereof which comprises reacting a compound of the Formula (II)

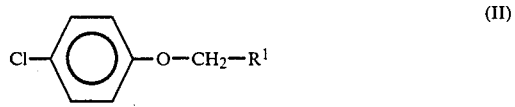

wherein
$R^1$ is carboxy, cyano, alkoxycarbonyl, halogenocarbonyl, 4-chlorophenoxyacetoxycarbonyl or a group of the Formula —COOMe$^I$ and
Me$^I$ is an alkaline metal or ammonium ion-
with a compound of the formula (III)

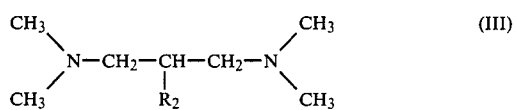

wherein
$R^2$ stands for hydroxy or halogen and optionally isolating the compound of the Formula (I) thus obtained from the reaction mixture in its acid addition salt preferably in the hydrochloric acid salt thereof.

The esterification reaction can be carried out by methods generally used and known per se (S. Pate: The Chemistry of Carboxylic Acids and Esters, Wiley, London, 1969). Thus e.g. the free carboxylic acid of the general Formula (II)-$R^1$ is carboxy) is reacted with an alcohol of the Formula (III) or a halogeno derivative thereof-$R^2$ is hydroxy or halogen, respectively) in a solvent medium. The free acid can also be replaced by the functional derivatives thereof, e.g. the corresponding nitrile ($R^1$ is cyano), anhydride-$R^1$ is 4-chloro-phenoxyacetoxycarbonyl-, halide-$R^1$ is halogenocarbonyl- or ester-$R^1$ is alkoxycarbonyl.

It is preferred to use 4-chlorophenoxyacetyl chloride or nitrile as the acid component and to carry out the reaction in an organic solvent as medium (benzene or xylene) at elevated temperatures and to use 1,3-bis-(dimethylamino)-2-propanol as the compound of the Formula (III). The reaction can be carried out at 60°-80° C. for 2-3 hours. The reaction product can be isolated from the reaction mixture advantageously in the form of the hydrochloric salt thereof.

The acute toxicity of the new compounds of the present invention was tested by administering it to male albino CFLP rats intraperitoneally and orally. The toxicity data obtained according to the method of Litchfield-Wilcoxon are as follows:

$LD_{50}$ i.p. = 700±42 mg/kg;

$LD_{50}$ per os = 2540±300 mg/kg.

The effect of the new compound of the Formula (I) on the lifespan was tested as well. The active ingredient was dissolved in physiological sodium chloride solution and administered i.p. to five CFY rats in a daily dose of 100 mg/kg. The average lifetime of the rats is as an average by about 5 months longer than that of the control group.

The effect of the new compounds of the present invention on the biological membranes—particularly on the cell membranes of the cerebral cortex—was determined. It has been found that in advanced age the microviscosity of the membranes of synaptosomes isolated from the cerebral cortex significantly increases. (The microviscosity was determined by measuring the fluorescence of anisotropy of membranes marked with diphenyl hexatriene). 24 months old CFY rats were treated with the active ingredient in a daily dose of 100 mg/kg i.p. for 20 days. As a result of this treatment the said parameter improved. It almost became identical with the value measured in one year old rats. This result is in complete conformity with the extension of the average lifetime.

The new compound of the present invention exerts an effect on the RNS synthesis of the brain-cells. The rate of the total and mRNS synthesis of the cells of cerebral cortex of old rats (24 months) is approximately twice less than that of the young and adult animals. As a result of a four weeks' treatment of the aged animals with the active ingredient (daily i.p. dose of 100 mg/kg) the synthesis of both RNS fractions accelerated significantly and speeded up almost to the rate of that of one year old animals.

On the basis of the above data it can be expected that the new compound according to the present invention stimulates the function of brain cells and thereby the mental activity (comprising the associating and learning ability), particularly in cases in which the said abilities are decreased either as a result of the natural ageing process or organic diseases, traumatic conditions or narcosis. The new compound of the present invention and acid addition salts thereof are therefore useful as neurostimulants or prophylactic agents preventing the functional, cerebral disorders induced by ageing (i.e. "antiaging" agent).

According to a further feature of the present invention there are provided pharmaceutical compositions comprising the new 1,3-bis-(dimethylamino)-2-propyl-4-chloro-phenoxy-acetate of the Formula (I) or a pharmaceutically acceptable acid addition salt thereof as active ingredient in admixture with suitable inert pharmaceutical carriers. The pharmaceutical compositions of the present invention can be administered in the form of tablets suitable for oral administration and comprises usual pharmaceutical carriers, auxiliary agents or additives, (e.g. talc, starch, cellulose etc.)

Pharmaceutical compositions suitable for oral administration can also be capsules or dragées. Pharmaceutical compositions suitable for i.v. administration can be prepared by dissolving the active ingredient in water, physiological sodium chloride solution or a physiologically acceptable organic solvent (e.g. various glycols.) Pharmaceutical compositions suitable for intramuscular application can be prepared by dissolving or suspending the active ingredient in a solvent discussed above. The solid compositions may generally contain 20-90% of the active ingredient while the active ingredient content of the solutions and suspensions amounts to 1-10% and 1-70%, respectively.

Further details of the present invention are to be found in the Examples without limiting the scope of protection to the said Examples.

EXAMPLE 1

13.0 g (0.063 moles) of 4-chlorophenoxyacetyl chloride are dissolved in 140 ml. of benzene. The solution is cooled to 0° C., whereupon 18.52 g (0.126 moles) of 1,3-bis(dimethylamino)-2-propanol are added dropwise at such a rate that the temperature should not exceed the 10° C. The addition having been completed the reaction mixture is refluxed for 3 hours and the solvent is evaporated in vacuo. The residual 1,3-bis(dimethylamino)-2-propyl-4-chlorophenoxyacetate is dissolved in a 10:1 mixture of diethyl ether and acetone and the hydrochloric acid salt is precipitated by introducing gaseous hydrogen chloride into the mixture. The precipitated crude product is filtered off, washed with ether and recrystallized from isopropanol. Yield: 21.0 g (85.5%). Mp.: 210°-212° C.

Analysis for the Formula $C_{15}H_{23}ClN_2O_3.2HCl$ (387.7), Calculated: C 46.46, H 6.50, N 7.22, Cl 27.43%; Found: C 45.42, H 6.56, N 7.70, Cl 28.26%.

$\lambda_{max}$ (methanol) 276 nm log ε: 1.5104.

IR (KBr): 2580 (amine salt), 1765 (ester-carbonyl) 1215, 1080 (aryl-alkyl-ether), 820 (aromatic group in position p) $cm^{-1}$.

$^1$H-NMR (DMSO): δ7.23–7.17 (m, aromatic), 5.71 (s, CH), 5.20 (s, O—CH$_2$), 3.47 (s, CH$_2$), 2.90 (s, CH$_3$).

EXAMPLE 2

6.5 g (0.032 moles) of 4-chlorophenoxyacetyl chloride are dissolved in 120 ml. of toluene. The solution is cooled to 0° C. and 9.4 g (0.064 moles) of 1,3-bis(dimethylamino)-2-propanol are added dropwise at a temperature less than 10° C. The reaction mixture is allowed to stand at 80°-82° C., for 3 hours, cooled to room temperature and the hydrochloric acid salt of 1,3-bis(dimethylamino)-2-propyl-4-chlorophenoxyacetate is precipitated by introducing gaseous hydrogen chloride. The crude product is filtered off, washed with isopropanol and recrystallized from isopropanol. Yield: 10.1 g (82.2%). Mp.: 209°-211° C. The other physical constants of the product are the same as referred in Example 1.

EXAMPLE 3

6.0 g (0.017 moles) of 4-chlorophenoxyacetic anhydride are dissolved in 70 ml. of benzene and 5.6 g (0.019 moles) of 1,3-bis(dimethylamino)-2-propanol are added dropwise at 5°–10° C. under stirring. The reaction mixture is boiled for 3 hours, whereupon the solvent is distilled off in vacuo. The residual 1,3-bis(dimethylamino)-2-propyl-4-chlorophenoxyacetate is dissolved in a 10:1 mixture of diethyl ether and acetone and the hydrochloric acid salt is precipitated with gaseous hydrogen chloride. The crude product is filtered off and recrystallized from isopropanol. Yield: 5.7 g (87.02%). Mp.: 209°–211° C. The other physical constants of the product correspond to those disclosed in Example 1.

EXAMPLE 4

15.0 g (0.085 moles) of 4-chlorophenoxyacetonitrile are dissolved in 80 ml. of toluene. To the solution 14.7 g (0.1 mole) of 1,3-bis(dimethylamino)-2-propanol and 2.0 ml. of 85% sulphuric acid are added at 5°–10° C. The reaction mixture is boiled for 4–5 hours, cooled to room temperature and neutralizedwith a sodium carbonate solution. The neutral phase is washed with water, dried and the hydrochloric acid salt of 1,3-bis-(dimethylamino)-2-propyl-4-chlorophenoxyacetate is precipitated upon introducing gaseous hydrogen chloride. The product is filtered off, dried and recrystallized from isopropanol. Yield: 25.67 g (78.2%). Mp.: 208°–210° C. The other physical constants of the product correspond to those disclosed in Example 1.

EXAMPLE 5

18.66 g (0.1 mole) of 4-chlorophenoxyacetic acid are dissolved in 40 ml. of isopropanol. A solution of 16.70 g (0.1 mole) of 1,3-bis-(dimethylamino)-2-chloropropane in isopropanol is added dropwise at 5°–10° C. The reaction mixture is heated to boiling for 2 hours, cooled, 200 ml. of diethyl ether are added and the hydrochloric acid salt of 1,3-bis-(dimethylamino)-2-propyl-4-chlorophenoxyacetate is precipitated upon introducing gaseous hydrogen chloride. The product is filtered off and washed with ether. Yield: 31.2 g (80.5%). Mp.: 208°–210° C.

The other physical constants of the product correspond to those disclosed in Example 1.

EXAMPLE 6

One proceeds according to Example 5 except that a solution of 20.86 g (0.1 mole) of the sodium salt of (4-chlorophenoxy)-acetic acid in 40 ml. of dimethyl formamide is used as acidic component. The dihydrochloride thus obtained (yield 30.62 g, 85%) is identical with that prepared according to Example 1.

EXAMPLE 7

A mixture of 10.0 g (0.05 moles) of methyl-4-chlorophenoxyacetate, 7.35 g (0.05 moles) of 1,3-bis(dimethylamino)-2-propanol, 1.9 g of sodium ethylate and 30 ml. of benzene is heated to boiling for 10 hours and the methanol formed is continuously distilled off from the reaction mixture as an azeotropic mixture formed with benzene. The residual solution is distilled off in vacuo, the residue is dissolved in a 10:1 mixture of diethyl ether and acetone and the hydrochloric acid salt of 1,3-bis-(dimethylamino)-2-propyl-4-chlorophenoxyacetate is precipitated upon introducing gaseous hydrogen chloride. The crude product is filtered off and recrystallized from isopropanol. Yield: 14.80 g (76.5%). Mp.: 207°–210° C. The other physical constants of the product are identical with those disclosed in Example 1.

EXAMPLE 8

Tablets comprising 250 mg of the active ingredient and having the following composition are prepared:

| Component | Amount, mg/tablet |
|---|---|
| Active ingredient | 250 |
| Lactose | 45 |
| Crystalline cellulose | 17 |
| Talc | 5 |
| Paraffine oil | 8 |

2500 g of crystalline active ingredient, 450 g of anhydrous lactose, and 170 g of anhydrous crystalline cellulose are homogenized with 80 g of paraffin oil and 350 ml. of anhydrous isopropanol in a homogenizer apparatus. The mass obtained is filtered, pressed through a sieve and the granules are dried. The dry substance is homogenized with 50 g of talc and the mixture is pressed into the form of tablets weighing 325 mg by a conventional tabletting machine.

EXAMPLE 9

Enterosolvent capsules or dragées are prepared by coating the product obtained according to Example 8 with an enterosolvent layer in a manner known per se.

EXAMPLE 10

Capsules having the following composition are prepared:

| Component | Amount, mg/capsule |
|---|---|
| Active ingredient | 250 |
| Known auxiliary agents | q.s. |

The active ingredient is homogenized with the additives and filled into hard gelatine capsules.

EXAMPLE 11

Powder capsules comprising 250 or 500 mg of the active ingredient are prepared. 250 mg or 500 mg of the active ingredient, respectively, are filled into powder ampoulles. The content of these ampoulles are diluted with 10 ml. of distilled water before use.

What we claim is:

1. 1,3-bis(dimethylamino)-2-propyl-4-chlorophenoxyacetate of the Formula (I)

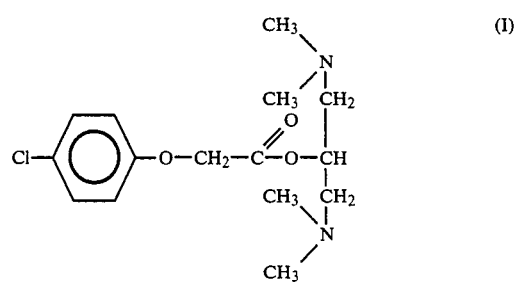

or a physiologically acceptable acid addition salt thereof.

2. 1,3-bis(dimethylamino)-2-propyl-4-chlorophenoxyacetatedihydrochloride.

3. A pharmaceutical composition for stimulating age-diminished cerebral functions comprising 1,3-bis(dimethylamino)-2-propyl-4-chlorophenoxyacetate or an acid addition salt thereof as active ingredients in admixture with suitable inert pharmaceutical carriers.

4. A method of stimulating age-diminished cerebral functions which comprises administering to a susceptible subject an effective amount of 1,3-bis-(dimethylamino)-2-propyl-4-chloro-phenoxy-acetate of the Formula (I) or an acid addition salt thereof.

* * * * *